(12) United States Patent
Endo et al.

(10) Patent No.: US 6,287,255 B1
(45) Date of Patent: Sep. 11, 2001

(54) APPARATUS FOR MEASURING TRANSPIRATION AMOUNT

(75) Inventors: Koji Endo; Yasushi Shioya, both of Tochigi; Masato Hoshi; Ryozo Nakai, both of Ichikai-machi, all of (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/418,430

(22) Filed: Oct. 15, 1999

(51) Int. Cl.[7] .................................................. A61B 5/00
(52) U.S. Cl. ........................ 600/307; 600/356; 600/573; 600/584; 73/29.01
(58) Field of Search ................................. 600/362–363, 600/345–346, 349, 356, 357, 372, 382–384, 573, 584, 307; 73/29.01

(56) References Cited

U.S. PATENT DOCUMENTS 4,066,068 * 1/1978 Nilsson et al. ..................... 600/307
4,461,303 * 7/1984 Refojo et al. ...................... 600/307

* cited by examiner

Primary Examiner—Robert L. Nasser
Assistant Examiner—Ryan Carter
(74) Attorney, Agent, or Firm—Oblon, Spivak, McClelland, Maier & Neustadt, P.C.

(57) ABSTRACT

Described is an apparatus for measuring a water transpiration amount, which comprises a barrel-type body having a humidity sensor inside of the body and opening portions on the top and bottom of the body, wherein a gas introductory path for feeding, from the outside of the apparatus, a gas having a predetermined water content to a surface to be measured is disposed at the side wall portion of the body and a freely openable or closable shutter is installed at the bottom opening portion of the body.

The apparatus according to the present invention makes it possible to carry out accurate and prompt measurement of a water amount transpired locally from the skin surface, ocular surface or the like without being influenced by the external circumstances such as wind.

10 Claims, 15 Drawing Sheets

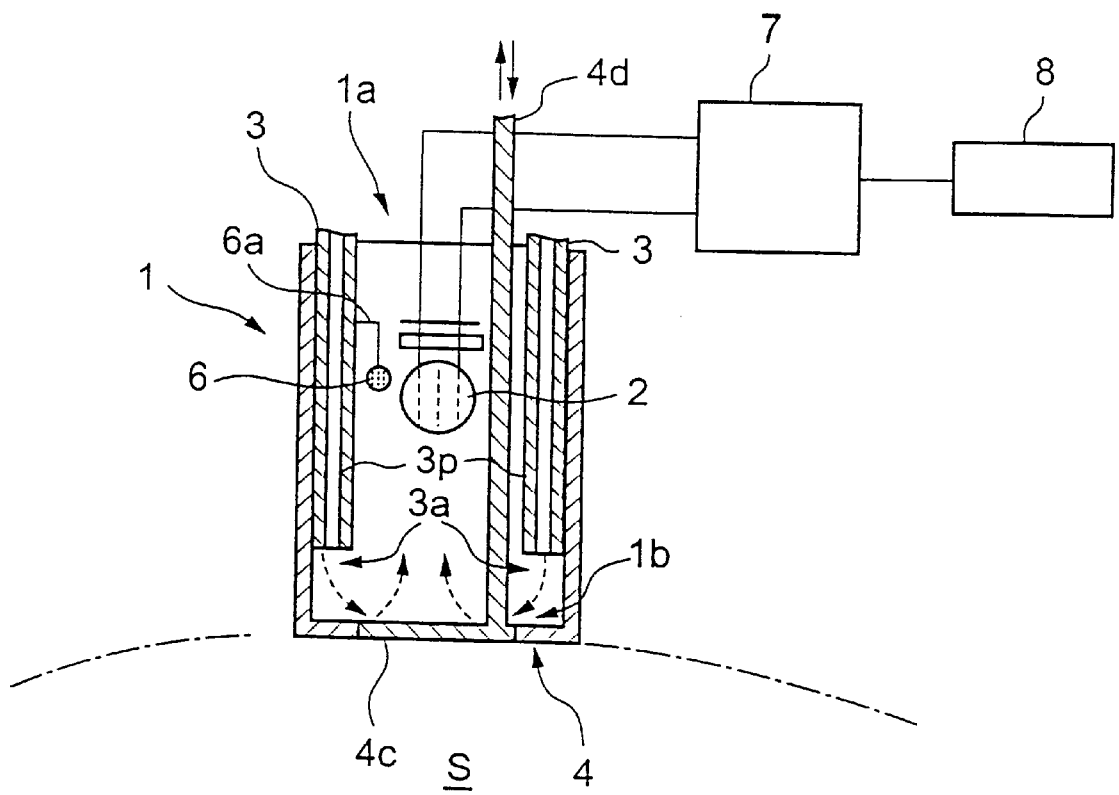
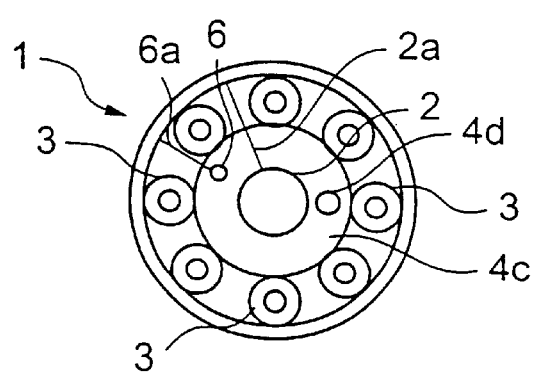
Fig. 13

Beginning of measurement

APPARATUS FOR MEASURING TRANSPIRATION AMOUNT

BACKGROUND OF THE INVENTION

1. Field of the Invention

This invention relates to an apparatus for measuring a transpiration amount, more specifically, to an apparatus suitable for measuring an amount of water transpired locally from the skin surface, ocular surface or the like.

2. Description of the Related Art

The amount of water transpired locally from the skin surface or the like has conventionally been determined using an apparatus, as illustrated in FIG. 19, comprising a cylindrical body 100 having an opened top and bottom; and two humidity sensors, that is, an upper humidity sensor 200 and a lower humidity sensor 300 disposed inside of the body. Described specifically, a water transpiration amount per unit time and unit area is determined from the difference between the values measured by these two humidity sensors 200 and 300 by making use of the fact that the water concentration at a position upwardly farther from the skin surface is smaller.

The conventional apparatus is however accompanied with the problem that owing to a tendency to be influenced by the external circumstances such as wind, it cannot be always used for measurement at a desired place and what is more important, stable data cannot be obtained easily. In addition, the conventional apparatus involves the drawback that it takes time as long as 1 minute or greater to complete measurement even if an automatic measuring instrument is connected to it, because the absence of a noise must be confirmed upon measurement. A large-scale apparatus is therefore necessary for measurement with excellent accuracy in a short time, but in practice, such an apparatus is utterly unsuited for local measurement of the skin surface or the like.

SUMMARY OF THE INVENTION

In view of the foregoing problems, the present invention has been completed. An object of the present invention is to provide a simple and convenient apparatus for measuring an amount of water transpired locally from the skin surface, ocular surface or the like, which apparatus makes it possible to acquire stable data in a short time without being influenced by the external circumstances such as wind.

The above-described object of the present invention is attained by an apparatus for measuring a transpiration amount, which comprises a barrel-type body having top and bottom opening portions and also having a humidity sensor inside of the body, wherein a gas introductory path for feeding, from the outside of the body, a gas having a predetermined water content to a surface to be measured inside of the body is disposed at the sidewall portion of the body, and a freely openable or closable shutter is installed at the bottom opening portion of the body.

When the invention apparatus for measuring a water transpiration amount is used, the apparatus is free from the influence of external circumstances such as wind because of a gas, which has a predetermined water content, filled inside of the barrel-type body 1; and accurate and noise-free measurement of a water transpiration amount from a surface to be measured such as skin surface can be conducted only by simple opening and closing operations of the shutter portion. It is accordingly possible to obtain stable data in a markedly short time, particularly in 10 seconds when an automatic measuring instrument is connected to the apparatus. As a result, this invention can be effectively applied and put into practical use for the evaluation of the relationship between skin condition and water transpiration amount, the evaluation of the barrier function of the skin, monitoring of perspiration, skin diagnosis at a shop front or the like.

In the present invention, particularly when an eye-surrounding attachment is installed, a closed space for the eye portion can be secured, which makes it possible to carry out accurate measurement of a water transpiration amount from the ocular surface which has so far been difficult in fact. As a result, the present invention can be effectively applied and put into practical use, for example, as a monitoring or diagnostic apparatus particularly for dry eyes.

BRIEF DESCRIPTION OF THE DRAWINGS

FIG. 12 is a schematic cross-sectional view illustrating an apparatus according to the third embodiment of the present invention; FIG. 13 is a schematic plan view illustrating the invention apparatus as illustrated in FIG. 12.

Figure 1:
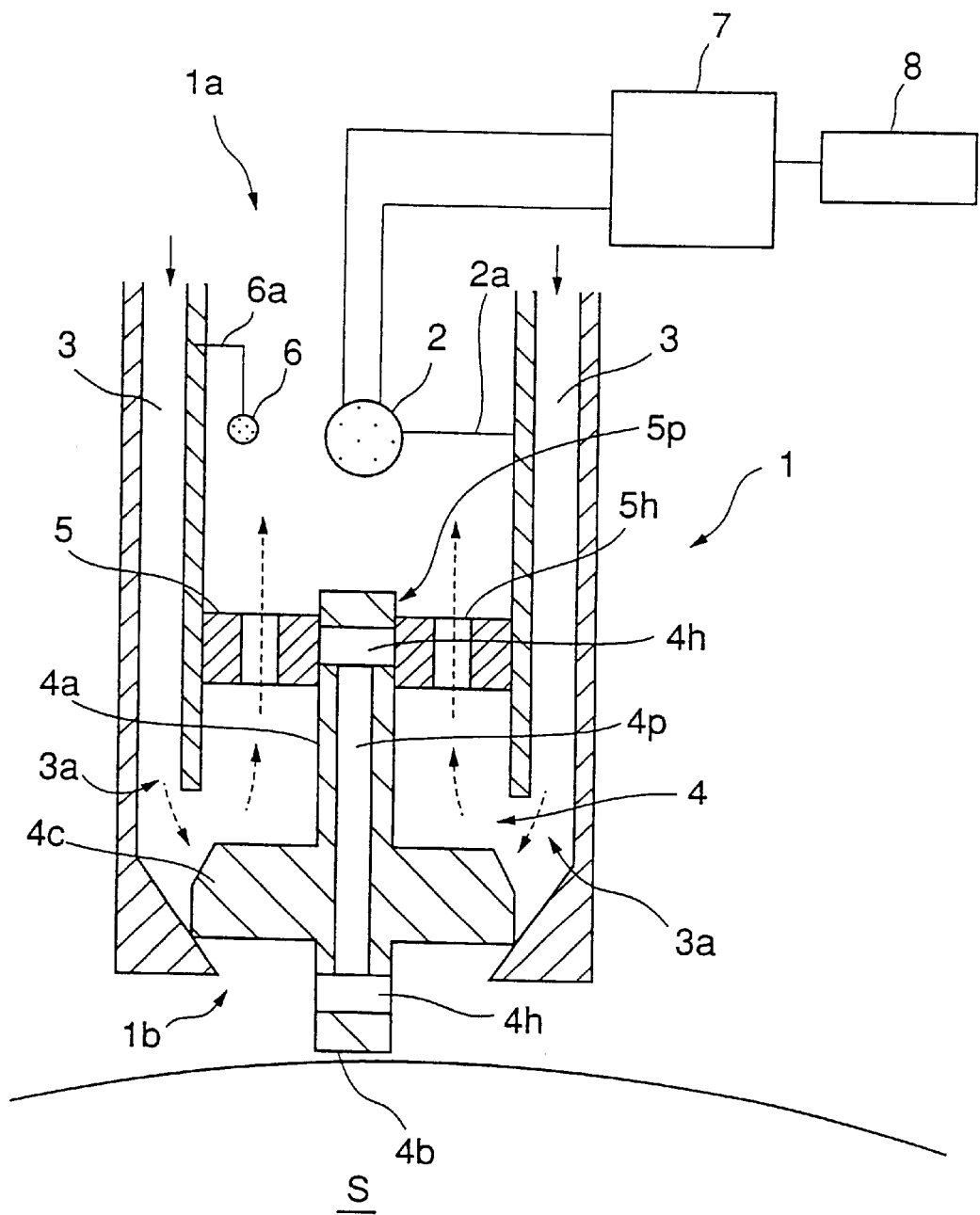
FIG. 1 is a schematic cross-sectional view illustrating an apparatus according to the first embodiment of the present invention which has been shut at the bottom opening portion.

[Legend]
1: barrel-type body
1a: top opening portion
1b: bottom opening portion
2: humidity sensor
3: gas introducing path
3a: opening portion 3*p*: pipe
4: shutter portion
4*a*: stem body
4*b*: lower end portion of the stem body
4*c*: lid portion
4*h*: air vent
4*p*: hollow portion
4*s*: rotary slide plate
4*t*: pin
5: supporting plate of the stem body
5*h*: air vent
6: temperature sensor
10: barrel-type body
20: humidity sensor
30: gas introductory path
31: gas collision plate
31*a*: gas exhaust port
32: doughnut-shaped pipe
32*a*: nozzle hole
32*b*: central cavity
40: temperature sensor
50: shutter portion
60: eye-surrounding attachment
S: surface to be measured
W: gas feeding space

DETAILED DESCRIPTION OF THE PREFERRED EMBODIMENTS

Although there is no limitation imposed on the specific shape of the barrel-shaped body usable in the present invention, for example, cylinder, square pillar or the like, that having an area, at the bottom opening portion, of about 0.2 to 10 cm$^2$ and a height of about 2 to 20 cm is preferred.

In the present invention, a humidity sensor is preferably disposed at a position higher than the opening portion of the gas introductory path inside of the barrel-type body in order to obtain stable measurement data. Although there is no limitation imposed on the nature of the humidity sensor, a quartz-crystal humidity sensor is particularly advantageous from the viewpoint of the measuring accuracy.

In the present invention, as the gas introductory path, that embedded in the side wall portion of the barrel-type body can be used insofar as it permits feeding of a gas having a predetermined water content to a surface to be measured such as skin surface. A gas introductory path formed by installing and fixing the necessary number of pipes, each of which opens at a position a little above the end of the bottom opening portion of the barrel-type body, to the sidewall surface inside of the barrel-type body is however convenient. Here, dry nitrogen, dry air or the like can be used as the gas having a predetermined water content.

In the present invention, a shutter portion having any specific structure, for example, an opening/closing shutter mechanism of a camera can be used insofar as the bottom opening portion of the barrel-type body can be opened or closed by it according to need. That having a rotary slide plate, which opens or closes the bottom opening portion, installed pivotally at the bottom of the barrel-type body or that comprising a vertically movable lid which opens or closes the bottom opening portion is simple in structure and excellent in operability.

In the present invention, it is preferred to dispose a temperature sensor inside of the barrel-type body, because it permits measurement of humidity with temperature as an index.

In the present invention, from a viewpoint of measuring a water transpiration amount particularly from the ocular surface, it is preferred to connectedly dispose a closed-space-forming eye-surrounding attachment at the bottom opening portion of the barrel-type body while interposing therebetween the above-described shutter portion.

In the present invention, it is preferred to form the bottom opening portion of the above-described eye-surrounding attachment, which is brought into contact with the surface of the face, into an oval shape so as to run along the outer periphery of the eye. The opening portion has preferably an area of about 5 to 20 cm$^2$. The area of the opening portion of the eye-surrounding attachment which is brought into contact with the surface of the face may be at least larger than the area of the single eye. Measurement can usually be carried out when the area is 5 to 100 cm$^2$. With a view to suppressing the influence of a water transpiration amount from the skin other than the ocular surface on the measurement value and to meeting the necessity of measuring transpiration amounts from right and left eyes respectively, the apparatus is desirably constructed to permit measurement of each eye. In this case, the opening portion having an area of 5 cm$^2$ or wider is necessary for not disturbing blink or ocular movement of the subject. If a difference in ocular size among individuals is taken into consideration, it is effective to select the area from a range of 5 to 20 cm$^2$.

In the present invention, the distance from the lower opening portion of the eye-surrounding attachment to be brought into contact with the face surface to the shutter portion, in other words, a distance formed by the eye-surrounding attachment above the eye portion is preferably adjusted to 0.5 to 3 cm. As a distance formed above the eye portion by the eye-surrounding attachment, at least 0.5 cm is sufficient for not disturbing blink or ocular movement of the subject upon measurement. In order to shorten a time lag from the initiation of the measurement by opening the shutter portion until the response of the humidity sensor and at the same time to exactly grasp the water transpiration behaviors of the eye such as blink, ocular movement and lacrimation, it is advantageous to decrease the volume of the portion surrounded by the face surface, eye-surrounding attachment and shutter portion. It is therefore effective to select the distance from a range of 0.5 to 3 cm as described above in consideration of the area of the opening portion of the eye-surrounding attachment.

In the present invention, when the eye-surrounding attachment is disposed in connection with the barrel-type body, desired as a gas introductory path is that equipped with a nozzle mechanism for filling a gas in the eye-surrounding attachment without direct gas injection to the ocular surface, because such a structure makes it possible to indirectly fill the gas in the eye-surrounding attachment without giving an unnecessary stimulus to the ocular surface.

Preferred examples of such a nozzle mechanism include that having a gas collision plate, which is equipped with a gas exhaust port, installed below the lower opening portion of the gas introductory path, with a gas-supplying space being disposed between the gas collision plate and the inside wall of the barrel-type body; and that having a doughnut-shaped pipe connected with the lower opening portion of the gas introductory path, said pipe having the necessary number of nozzle holes opened toward the inside wall of the eye-surrounding attachment. It is not always necessary to dispose the gas collision plate or doughnut-shaped pipe inside of the barrel-type body. It may be disposed inside of the eye-surrounding attachment.

EXAMPLES

The present invention will hereinafter be described in further detail with reference to accompanying drawings illustrating the following embodiments.

Figure 2:
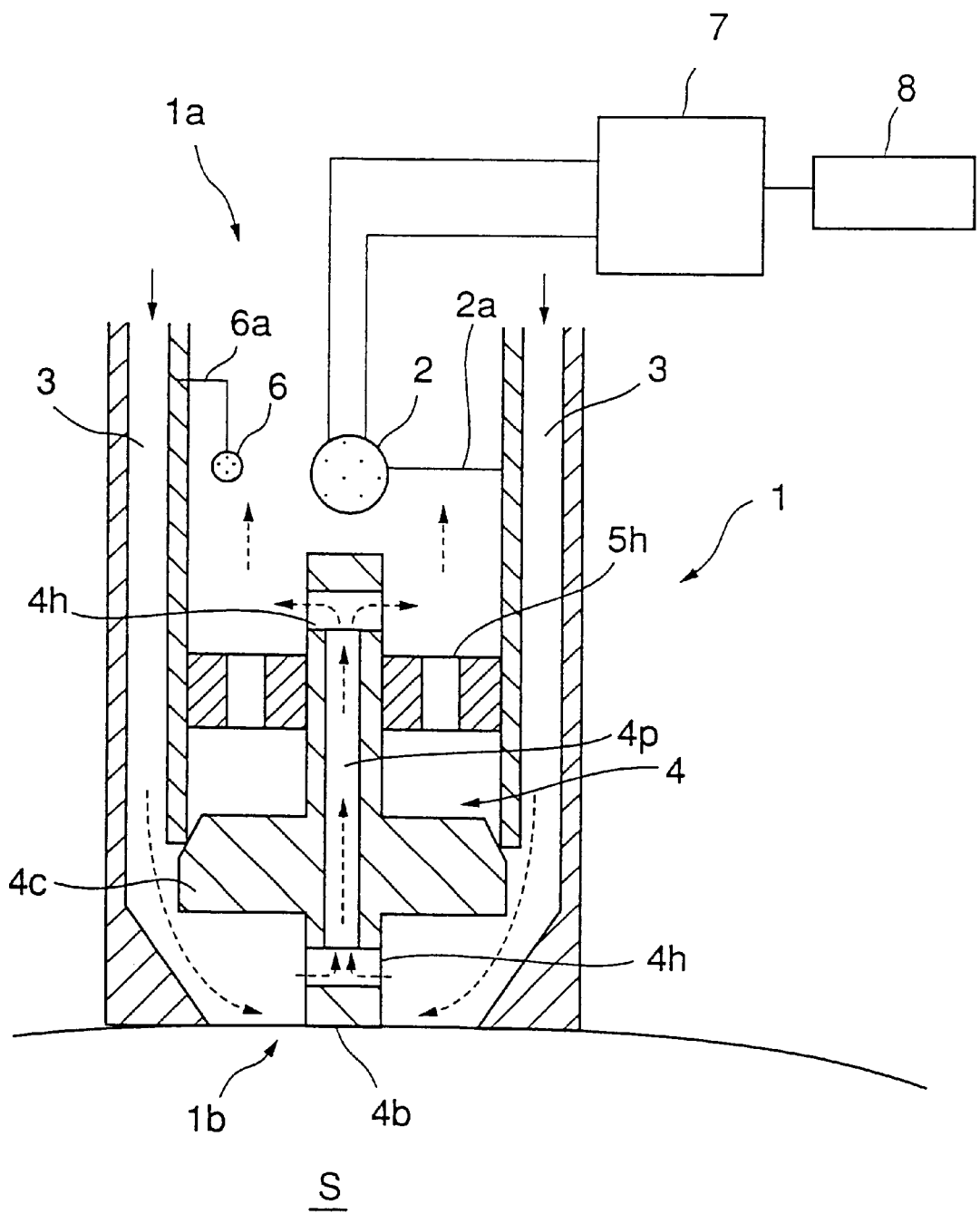
FIG. 2 is a schematic cross-sectional view of the invention apparatus as illustrated in FIG. 1, which has however been opened at the bottom opening portion.

FIGS. 1 and 2 each illustrates the first embodiment of the present invention. Referring to FIGS. 1 and 2, indicated at numeral 1 is a barrel-type body in the cylindrical form (having an inner diameter of 2 cm and a height of 4 cm) having, at the top and bottom thereof, opening portions 1*a* and 1*b*, respectively. A humidity sensor 2 is disposed via a supporting rod 2*a* at the lateral center and a little above the longitudinal center.

Indicated at numeral 3 is a gas introductory path. It is disposed at the side wall portion of the barrel-type body 1. Its opening portion 3*a* opens downward at the position a little above the end of the bottom opening portion 1*b* of the barrel-type body 1. Through it, a gas having a predetermined water content is introduced into the barrel-type body 1, for example, from an external gas tank (not illustrated) connected with the gas introductory path and then fed to a surface S to be measured such as skin surface.

Indicated at numeral 4 is a shutter portion composed of a stem body 4*a*, a lower end portion 4*b* and a lid portion 4*c* which is protrusively disposed in the collar form at the outer periphery of the stem body a little above the lower end portion 4*b*, more specifically, above the lower end portion 4*b* by a distance corresponding to one vertical stroke and has a diameter larger than that of the bottom opening portion 1*b* of the barrel-type body 1. This shutter portion 4 is insertedly placed inside of the barrel-type body 1 by inserting and supporting the upper portion of the stem body 4 in a central through-hole 5*p* of a stem-body supporting plate 5, which has been laterally installed inside of the barrel-type body 1, while assuring free vertical movement of the shutter portion. The bottom opening portion 1*b* of the barrel-type body 1 can therefore be opened or closed freely by the vertical movement of the stem body 4*a*.

The vertical movement of the stem body 4*a* can be controlled by any means. For example, a controlling system making use of expansion and contraction properties of a spring installed in the upper portion of the stem body 4*a* is convenient and therefore preferred.

Figure 3:
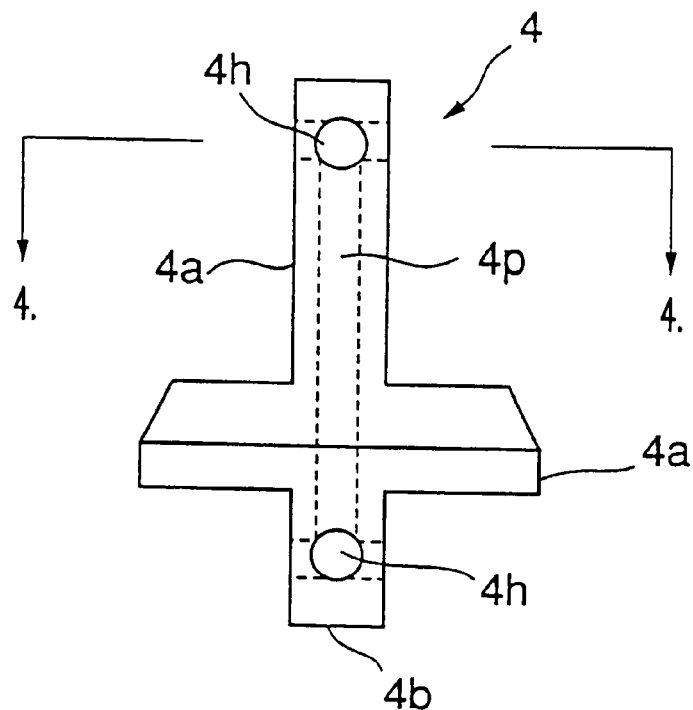
FIG. 3 is a front explanatory view illustrating the shutter portion.
Figure 4:
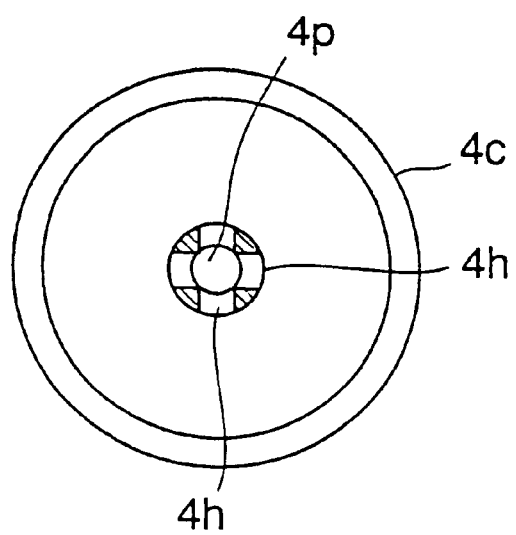
FIG. 4 is a cross-sectional explanatory view taken along line I—I of FIG. 3.

Inside of the stem body 4*a*, a hollow portion 4*p* which runs along the axial direction of the stem body and a plurality of vent holes 4*h* which run along the diameter-wise direction and are communicated each other at the upper and lower end portions of the hollow portion are disposed as illustrated in FIGS. 2 to 4 so as to release, above the stem-body supporting plate 5, a gas fed inside of the barrel-type body 1 when the bottom opening portion 1*b* of the barrel-type body 1 is opened.

Figure 5:
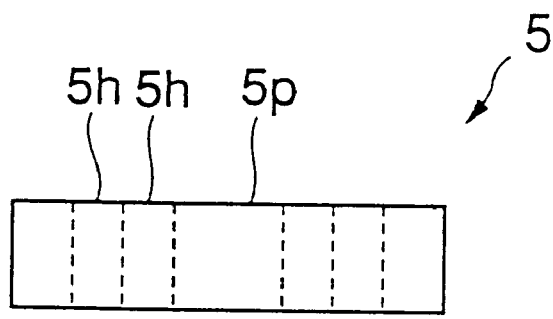
FIG. 5 is a front explanatory view illustrating a supporting plate of a stem body.
Figure 6:
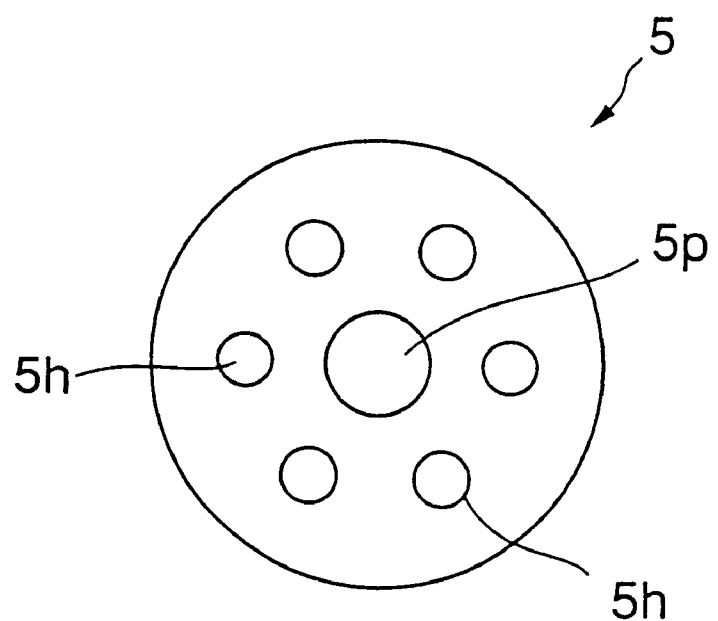
FIG. 6 is a plan explanatory view illustrating the supporting plate of the stem body.

The stem-body supporting plate 5 has a plurality of vent holes 5*h* disposed as illustrated in FIGS. 1, 5 and 6 so as to release, above the stem-body supporting plate 5, a gas fed inside of the barrel-type body 1 when the bottom opening portion 1*b* the barrel-type body 1 is closed.

Indicated at numeral 6 is a temperature sensor which is disposed as needed through a supporting rod 6 in the vicinity of the humidity sensor 2 inside of the barrel-type body 1 and facilitates the measurement of humidity at the optimum temperature.

Indicated at numeral 7 is an automatic measuring instrument which is connected with the humidity sensor 2 and automatically calculates a water transpiration amount from the data detected by the humidity sensor 2. Indicated at 8 is a recorder for automatically recording the measuring results. The connected disposal of these automatic measuring instrument 7 and recorder 8 make it possible to obtain measurement data only in 10 seconds and at the same time, to monitor a time-dependent change.

Next, a measuring method by using the apparatus of FIGS. 1 and 2 according to the first embodiment of the present invention will be described.

As illustrated in FIG. 1, this apparatus is held in the vicinity of the surface S to be measured such as skin surface with the shutter portion 4 being pulled down, for example, by the action of a spring, in other words, with the lid portion 4*c* being engaged with the inner edge portion of the bottom opening portion 1*b* of the barrel-type body 1 and therefore with the bottom opening portion 1*b* being closed. Under such closed condition, humidity is measured by the humidity sensor 2, while a gas having predetermined water content is injected and fed (arrows in FIG. 1) into the barrel-type body 1 through the gas introductory path 3. Incidentally, the gas fed inside of the barrel-type body 1 is discharged as needed from the top opening portion 1*a* of the barrel-type body through the air vent 5*h*. Then, as illustrated in FIG. 2, the bottom opening portion 1*b* of the barrel-type body 1 is pressed against the surface S to be measured. By the contact with the surface S, the lower end portion 4*b* of the stem body 4*a* is pushed upward, followed by the upward movement of the lid portion 4*c*. The bottom opening portion 1*b* is then opened, whereby the surface S is exposed inside of the barrel-type body 1. Under this condition, humidity is measured by the humidity sensor 2 while a gas having a predetermined water content is injected and fed to the exposed surface (arrows in FIG. 2) and based on the difference from the previously measured value, that is, an increase in the humidity, a water transpiration amount is determined. Incidentally, the gas fed inside of the barrel-type body 1 is discharged as needed from the top opening portion 1*a* of the barrel-type body 1 through the air vent 4*h* and hollow portion 4*p*.

Figure 7:
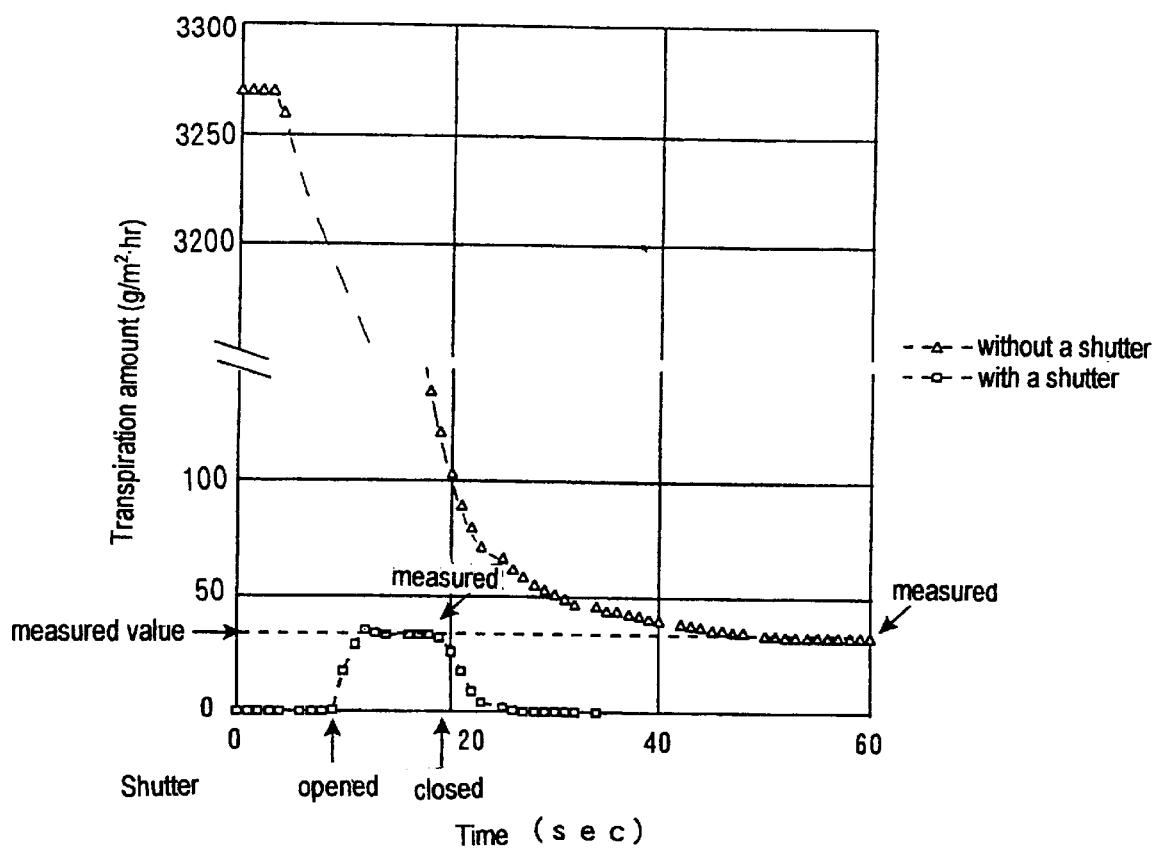
FIG. 7 is a graph showing measuring results using the invention apparatus as illustrated in FIGS. 1 and 2 and the similar apparatus except for the removal of the shutter.
Figure 8:
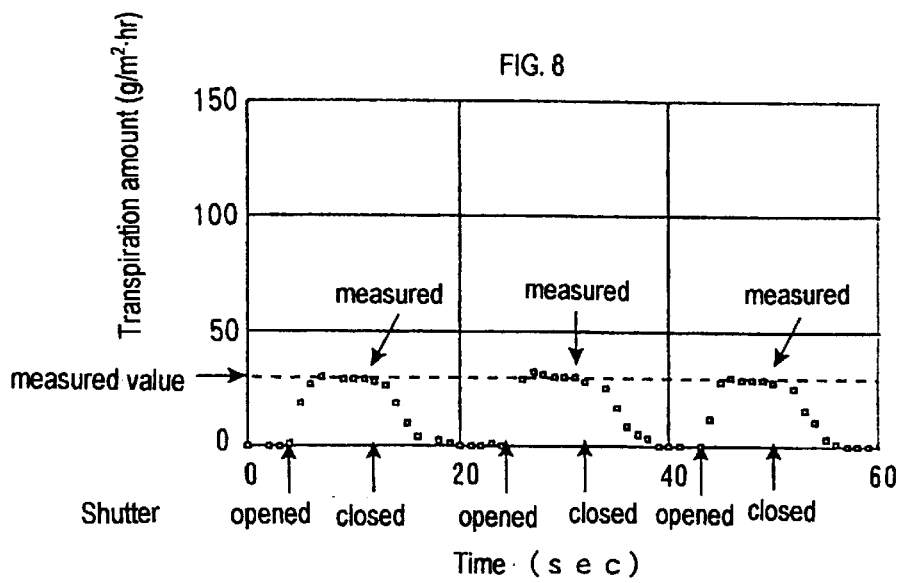
FIG. 8 is a graph illustrating the measuring results of the same site in repetition for 60 seconds by using the invention apparatus as illustrated in FIGS. 1 and 2.

For reference, the water transpiration amount of a human forehead was measured using the apparatus of FIGS. 1 and 2 according to this embodiment of the present invention and a similar apparatus except for the removal of the shutter portion. Results were as shown in FIG. 7. As is apparent from FIG. 7, the apparatus free from a shutter portion was influenced by the external circumstances and it took about 60 seconds to obtain a stable response from the humidity sensor, while the invention apparatus having a shutter installed therein brought about similar results to the conventional apparatus only 10 seconds after the shutter was opened.

In addition, when the invention apparatus was used, humidity was measured three times at the same site (human forehead) during only 60 seconds and moreover, the results thus obtained were stable.

Figure 9:
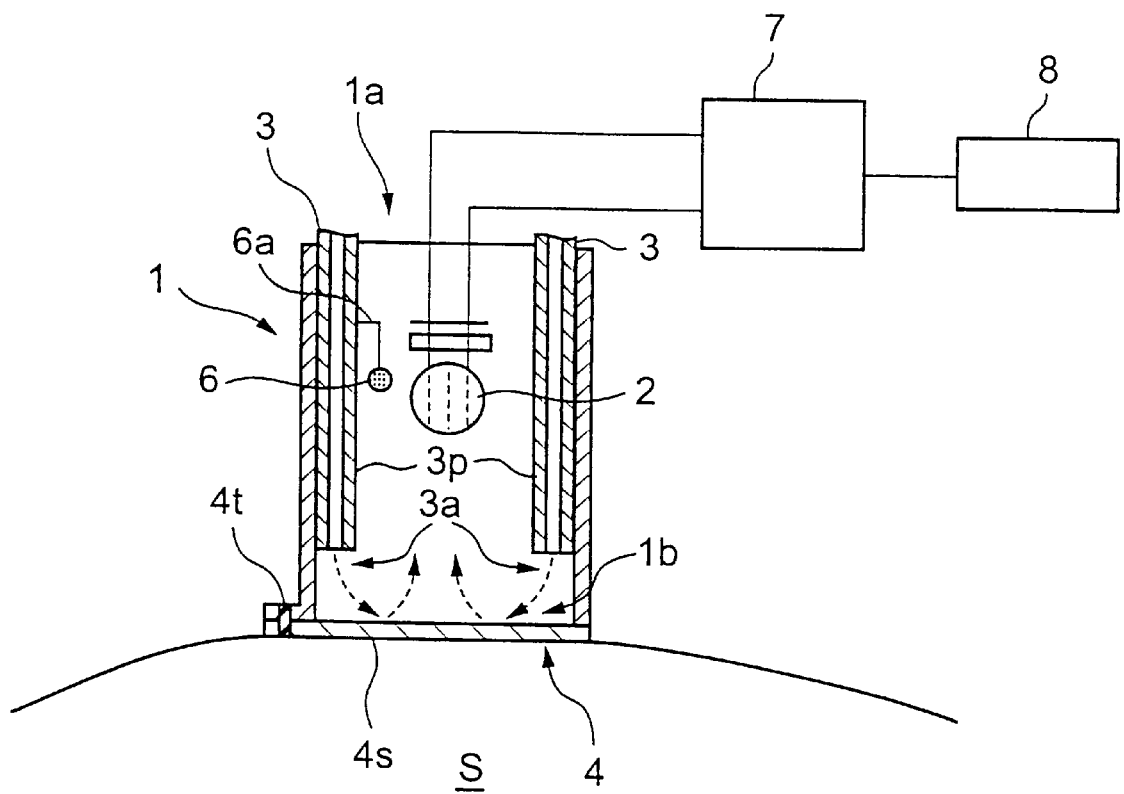
FIG. 9 is a schematic cross-sectional view illustrating an apparatus according to the second embodiment of the present invention which has been shut at the bottom opening portion.
Figure 10:
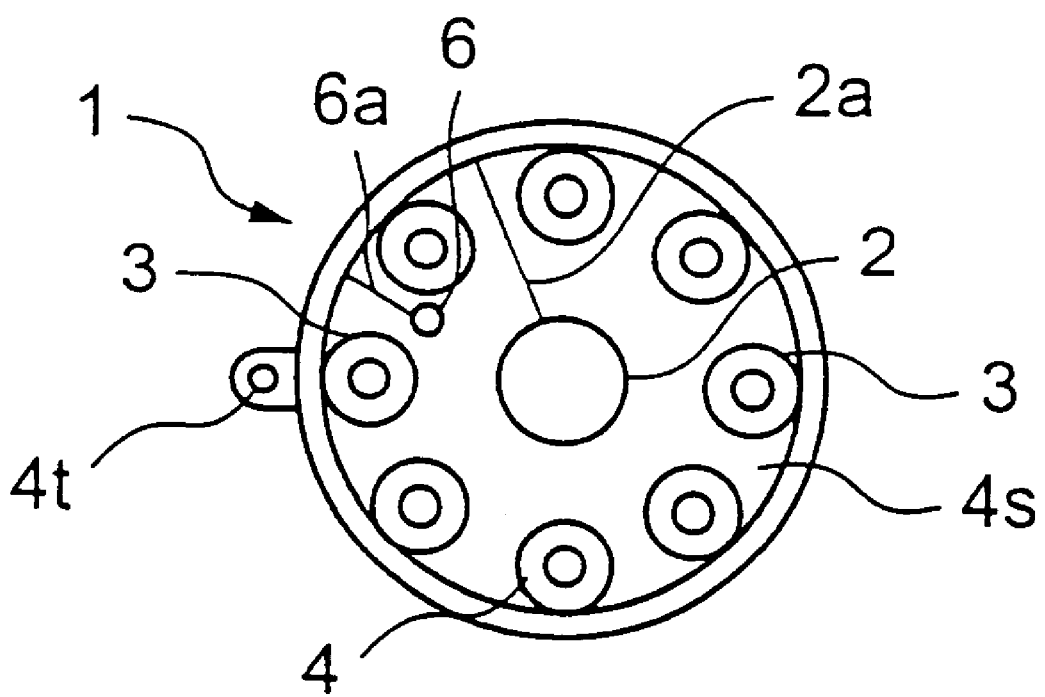
FIG. 10 is a schematic plan view illustrating the invention apparatus as illustrated in FIG. 9.
Figure 11:
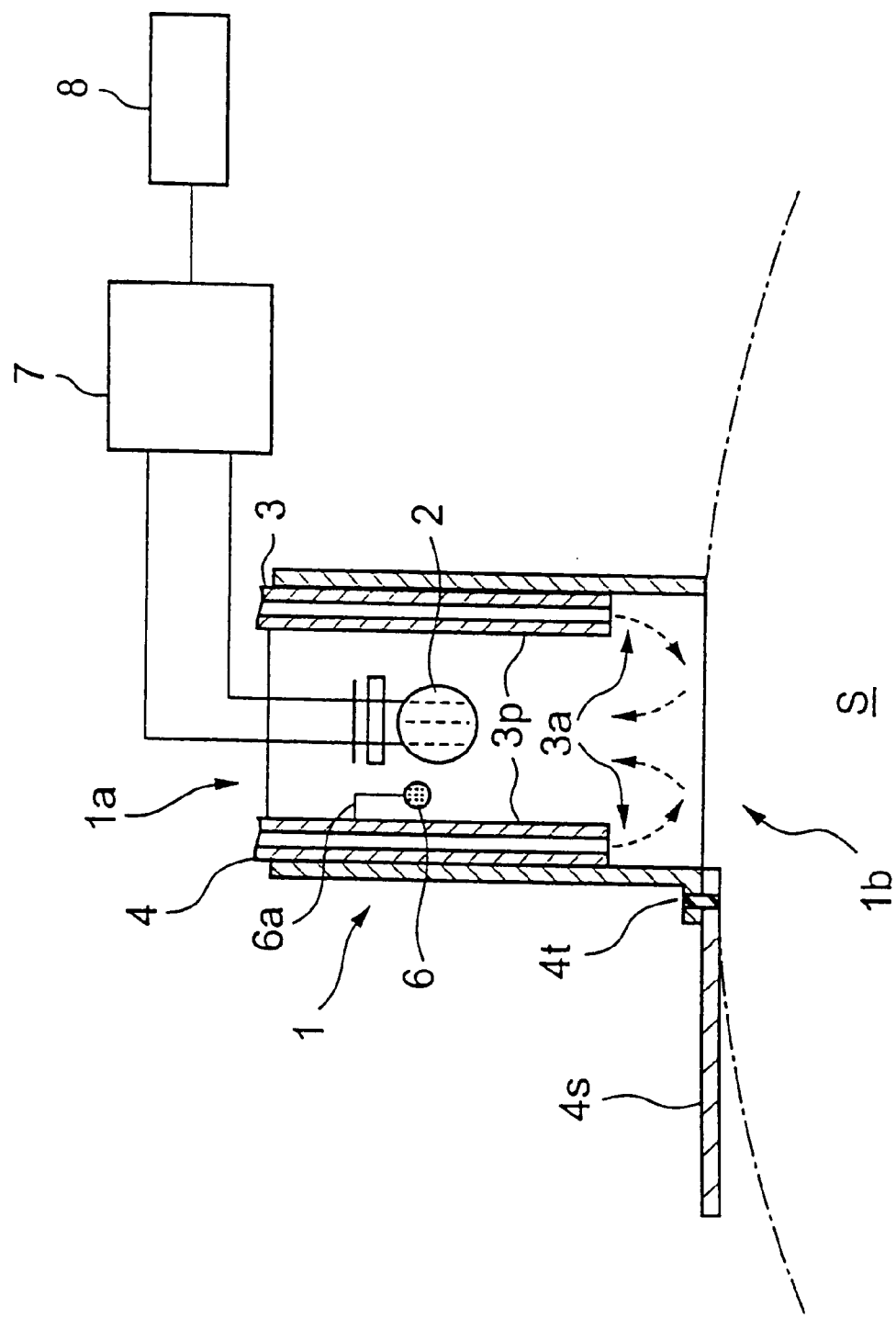
FIG. 11 is a schematic cross-sectional view illustrating the invention apparatus as illustrated in FIG. 9, which has however been opened at the bottom opening portion.

FIGS. 9 to 11 illustrate the apparatus according to the second embodiment. Referring to FIGS. 9 to 11, a humidity sensor 2 and temperature sensor 6 are installed inside of a barrel-type body 1 having top and bottom opening portions 1*a* and 1*b*, similar to the first embodiment.

Indicated at numeral 3 is a gas introductory path. Eight pipes 3*p* are installed and fixed to the inside surface of the barrel-type body 1. Each of them has an opening portion 3*a* which opens downward at the position a little above (about 7 mm) the end of the bottom opening portion 1*b* of the barrel-type body 1. This gas introductory path makes it possible to introduce a gas having a predetermined water content into the barrel-type body 1, for example, from an external gas tank (not illustrated) connected with the gas introductory path and feed it to the surface S to be measured such as skin surface by injection.

Indicated at numeral 4 is a shutter portion wherein a rotary slide plate 4*s* pivotally installed to the bottom portion of the barrel-type body 1 with a pin 4t, which makes it possible to freely open or close the bottom opening portion 1b of the barrel-type body 1.

Next, a measuring method using the invention apparatus of FIGS. 9 to 11 according to this second embodiment will be described.

First, the bottom opening portion 1b of the barrel-type body 1 is pressed against the surface S to be measured such as skin surface with the shutter portion 4 being closed and, under the closed condition, humidity is measured by the humidity sensor 3 while a gas having a predetermined water content is injected and fed (arrows in FIG. 9) into the barrel-type body 1 through the gas introductory path 3. Then, the bottom opening portion 1b is opened by turning the rotary slide plate 4s of the shutter portion 4 to expose the surface S in the barrel-type body 1. While a gas having predetermined water content is injected and fed (arrows in FIG. 11) to the exposed surface, humidity is measured by the humidity sensor 3. Based on the difference from the previously measured value, that is, an increase in humidity, the water transpiration amount is determined. Incidentally, the gas fed to the barrel-type body 1 is discharged as needed from the top opening portion 1a of the barrel-type body 1.

FIGS. 12 and 13 illustrate an apparatus according to the third embodiment, wherein instead of the shutter portion 4 of the second embodiment which is opened by a rotary slide plate, a lid portion 4c is disposed in connection with the lower end portion of a supporting rod 4d which moves freely in the vertical direction. This structure makes it possible to freely open and close the bottom opening portion 1b of the barrel-type body 1.

Figure 14:
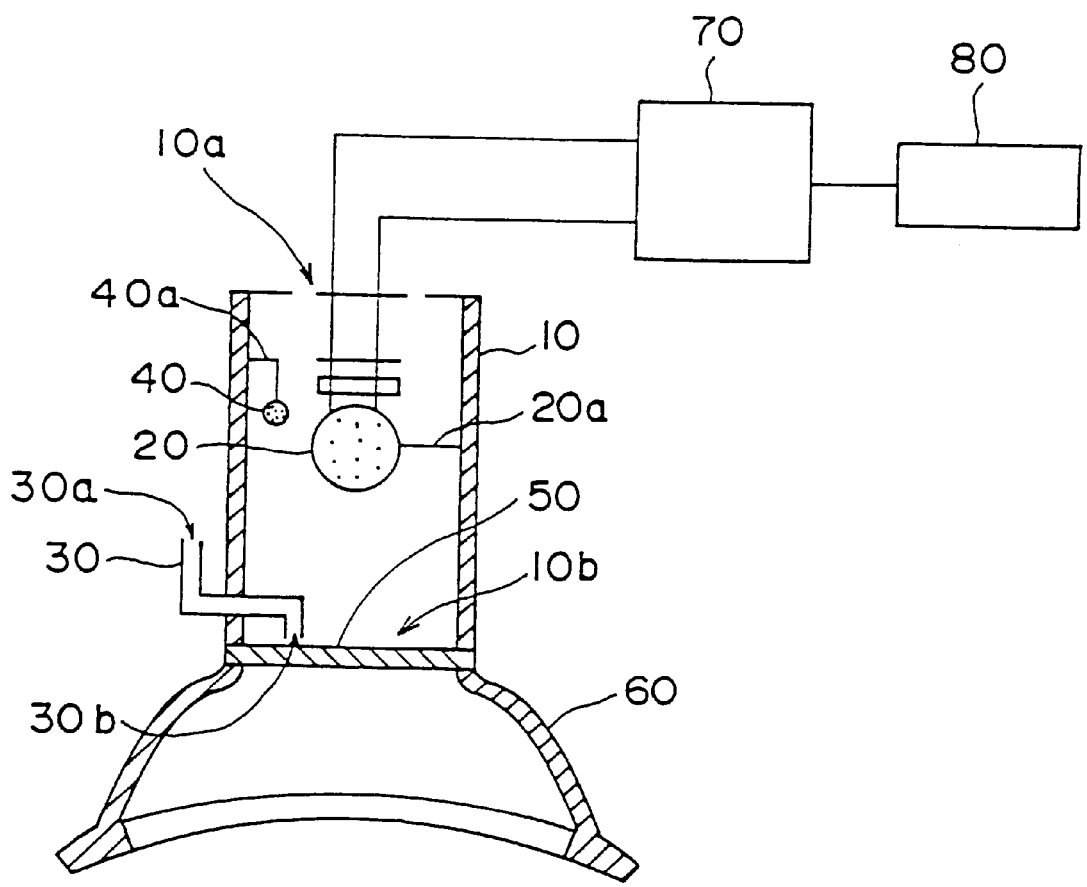
FIG. 14 is a schematic cross-sectional view illustrating an apparatus according to the fourth embodiment of the present invention.

FIG. 14 illustrates an apparatus according to the fourth embodiment. Referring to FIG. 14, indicated at numeral 10 is a cylindrical body (having an inner diameter of 2 cm and a height of 4 cm) having the top and bottom opening portions 10a and 10b. At the lateral center and a little above the longitudinal center, a humidity sensor 20 is disposed via a proper supporting rod 20. At the side wall portion of the cylindrical body, disposed is a gas introductory path 30, through which a gas having a predetermined water content is introduced, for example, from an external gas tank (not illustrated) connected with the path into the cylindrical body 10 and an eye-surrounding attachment 60 which will be described later and then fed to an eye portion to be measured. Indicated at numeral 40 is a temperature sensor disposed as needed in the vicinity of the humidity sensor 20 in the cylindrical body 10 through a supporting rod 40a, which facilitates measurement of humidity at the optimum temperature.

Indicated at numeral 50 is a sliding type shutter portion disposed at the bottom opening portion 10b of the cylindrical body 10, by which the bottom opening portion 10b can be opened or closed freely.

Indicated at numeral 60 is an eye-surrounding attachment. It has a bowl shape composed of an oval lower opening portion (having a longer diameter of 5 cm and a shorter diameter of 3 cm) which curves along the eye (single eye) and an upper opening portion communicated with the bottom opening portion 10b of the cylindrical body 10. This attachment is disposed in connection with the bottom opening portion 10b of the cylindrical body 10 with the shutter portion 50 being interposed therebetween. Such a structure makes it possible to cover the upper portion of the eye while forming a space of about 1 cm between the lower end of the shutter portion 50 and the eye and to fill the inside of the space with a gas from the air introductory path 50.

Indicated at numeral 70 is an automatic measuring instrument which is connected with the humidity sensor 20 and automatically calculates a water transpiration amount based on the data detected by the humidity sensor 20. Indicated at numeral 80 is a recorder for automatically recording the measurement results. Disposal of these automatic measuring instrument 70 and recorder 80 makes it possible to obtain measurement data only in 10 seconds similar to the first embodiment and at the same time, to monitor a time-dependent change.

Figure 15:
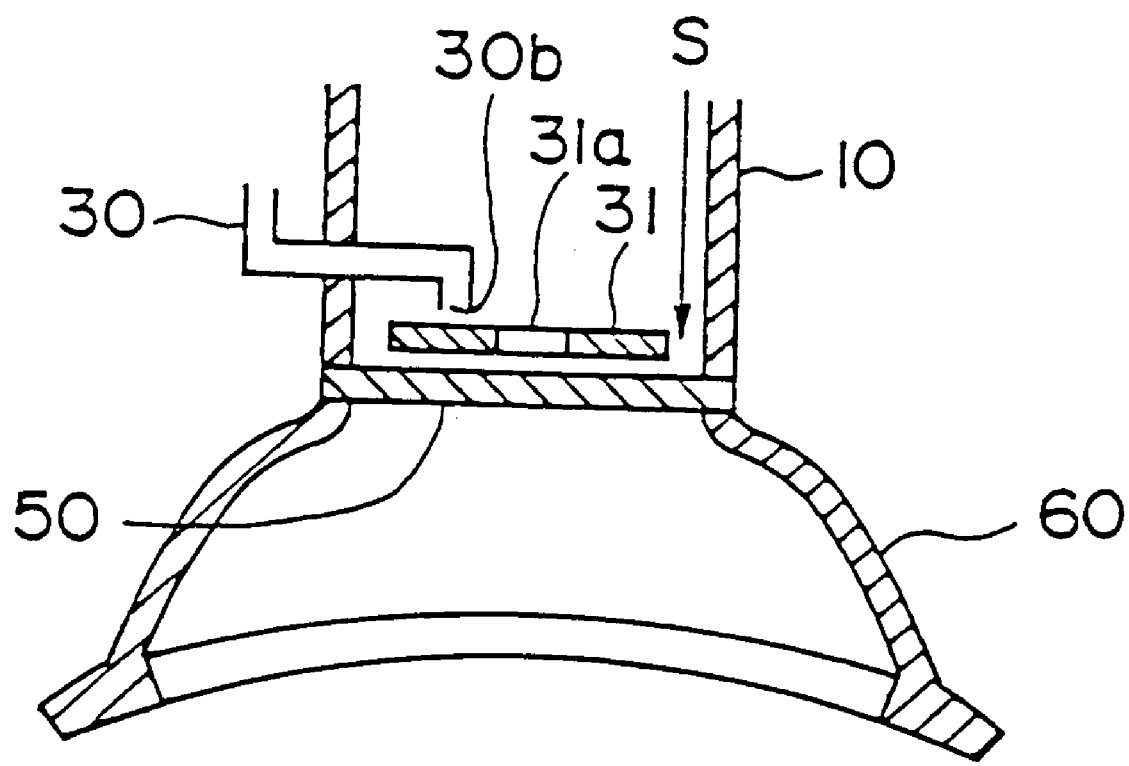
FIG. 15 is a schematic cross-sectional view illustrating an apparatus according to the fifth embodiment of the present invention.

FIG. 15 illustrates an apparatus according to the fifth embodiment, wherein below the lower opening portion 30b of the air introductory path 30 in the fourth embodiment, a gas collision plate 31 having a gas exhaust port 31a above the ocular surface is installed with a gas feeding space W being disposed between the gas collision plate and the inside wall of the cylindrical body 10. Such a structure makes it possible to fill a gas in the eye-surrounding attachment without direct injection of the gas to the ocular surface and at the same time, to send the gas to the cylindrical body 10 through the gas exhaust port 31a after filling.

Figure 16A:
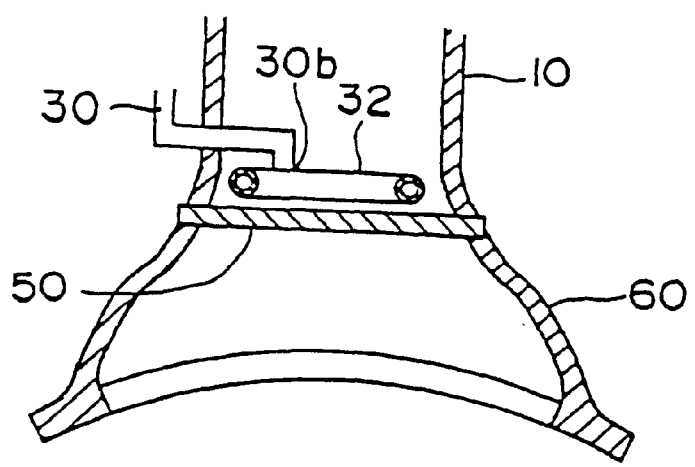
FIG. 16 illustrates an apparatus according to the sixth embodiment of the present invention, wherein (1) is its schematic cross-sectional view; (2) is a bottom explanatory view of a doughnut-shaped pipe and (3) is an enlarged cross-sectional explanatory view illustrating a nozzle hole portion of the doughnut-shaped pipe.
Figure 16B:
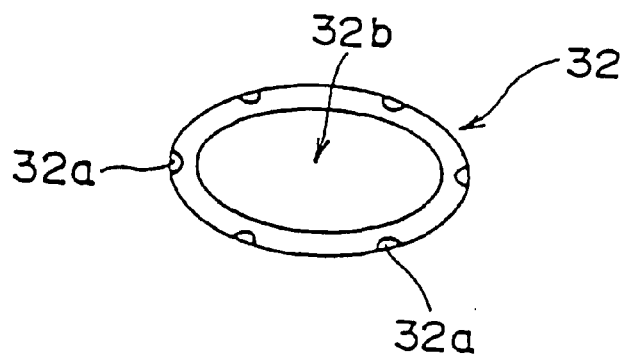
Figure 16C:
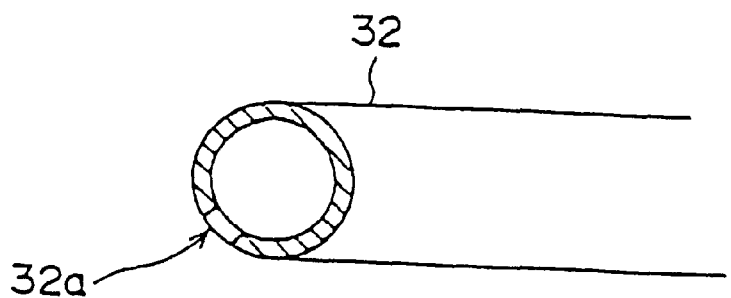

FIG. 16 illustrates an apparatus according to the sixth embodiment wherein a doughnut-like pipe 32 which has the necessary number of nozzle holes 32a and is opened in the inner side wall direction of the eye-surrounding attachment is connected with the lower opening portion 30b of the gas introductory path 30 of the fourth embodiment. Such a structure makes it possible no only to fill the gas in the eye-surrounding attachment but also to send the gas to the cylindrical body 10 through the central cavity 32b after filling.

A description will next be made of a measuring method using each of the invention apparatuses according to the embodiments as illustrated in FIGS. 14 to 16.

With the bottom opening portion 10b of the cylindrical body 10 being closed by the shutter portion 50, the eye-surrounding attachment 60 is pressed against the eye portion (single eye). Under the closed condition, humidity is measured by the humidity sensor 20 while a gas having a predetermined water content is injected and fed to the cylindrical body 10 through the gas introductory path 30. Then, the bottom opening portion 10b is opened by moving the shutter portion 50 to expose the eye portion (single eye) inside of the cylindrical body 10. Under the eye-closed condition, humidity is measured by the humidity sensor 20 while a gas having a predetermined water content is injected and fed in the eye-surrounding attachment 60. After confirmation that the measured value becomes stable, the eye is opened and measurement is continued further without disturbing the free blinking of the eye. A water transpiration amount is found from the difference between these measured values, that is, an increase in humidity. Incidentally, the gas fed in the cylindrical body 10 is discharged as needed from the top opening portion 10a of the cylindrical body 10.

Upon measurement, in the embodiment as illustrated in FIG. 15, the gas injected and fed from the gas introductory path 30 is not injected directly to the ocular surface owing to the presence of the gas collision plate 31 but fed along the inner side-wall portion of the eye-surrounding attachment 60 from the gas feeding space W and filled in the attachment so that the gas does not give unnecessary stimulation to the ocular surface. The gas, after brought into contact with the ocular surface, is smoothly sent to the humidity sensor 20 of the cylindrical body 10 through the gas exhaust port 31a.

In the embodiment as illustrated in FIG. 16, the gas is injected and fed toward the inside wall of the eye-surrounding attachment 60 through nozzle holes 32a of the doughnut-like pipe 32 connected with the gas introductory path 30 and is not injected directly to the ocular surface so that unnecessary stimulation to the ocular surface can be prevented. After brought into contact with the ocular surface, the gas is smoothly sent to the humidity sensor 20 of the cylindrical body 10 through the central cavity 32b of the doughnut-like pipe 32.

Figure 17:
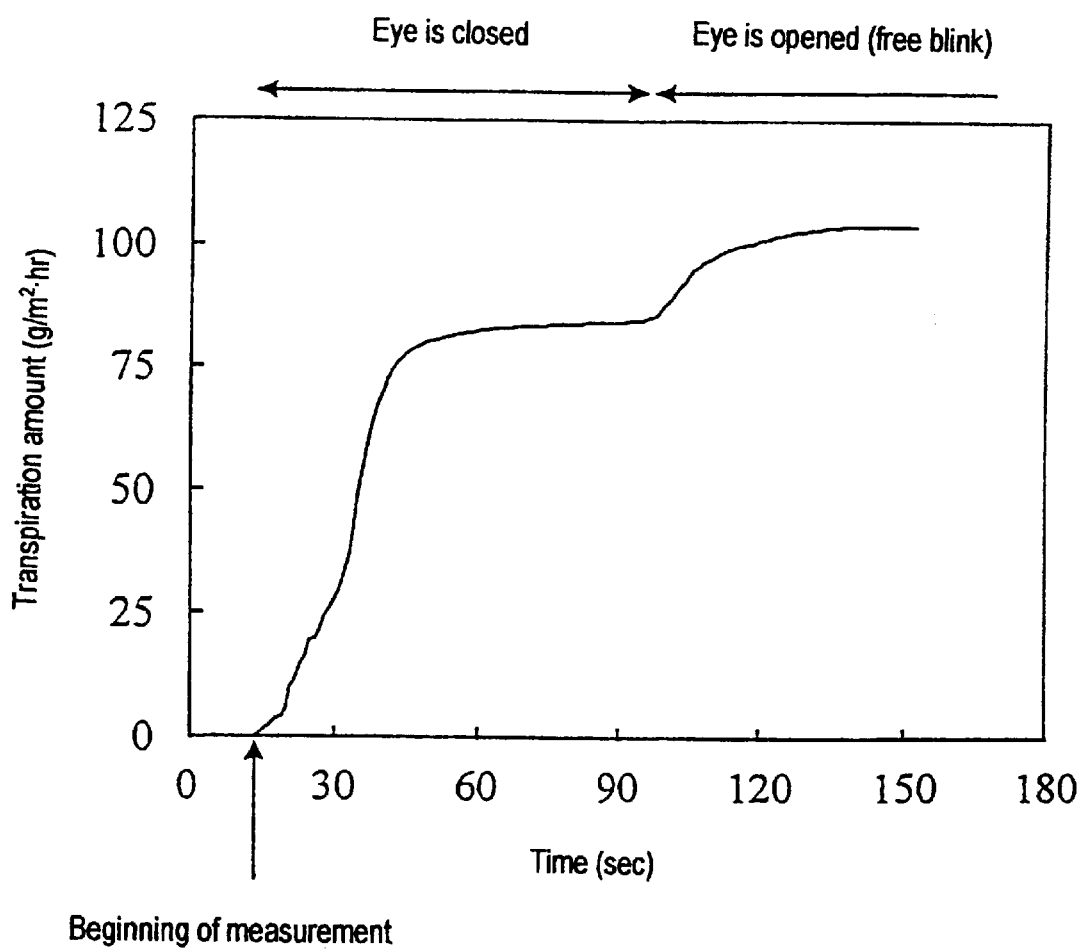
FIG. 17 is a graph showing measuring results using the invention apparatus of FIG. 15.

The results of the water transpiration amount from the ocular surface measured in accordance with the above-described method by using the apparatus according to the embodiment as illustrated in FIG. 15 are shown in FIG. 17. From FIG. 17, it is apparent that the water transpiration amount shows an increase when the eye is opened. The present invention makes it possible to carry out accurate measurement of water transpiration behaviors from the ocular surface which has so far been difficult in fact.

Figure 18:
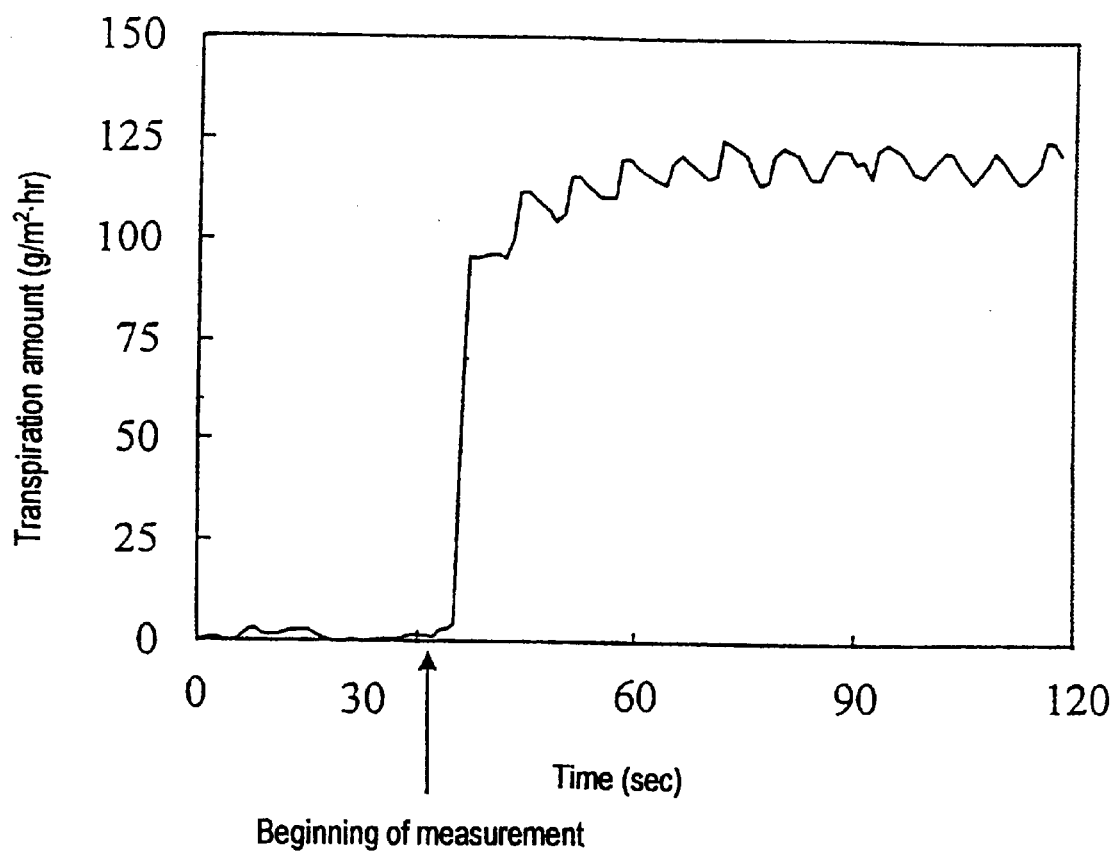
FIG. 18 is a graph showing the results of measuring a transpiration amount by the invention apparatus of FIG. 15 upon blinking at predetermined intervals.
Figure 19:
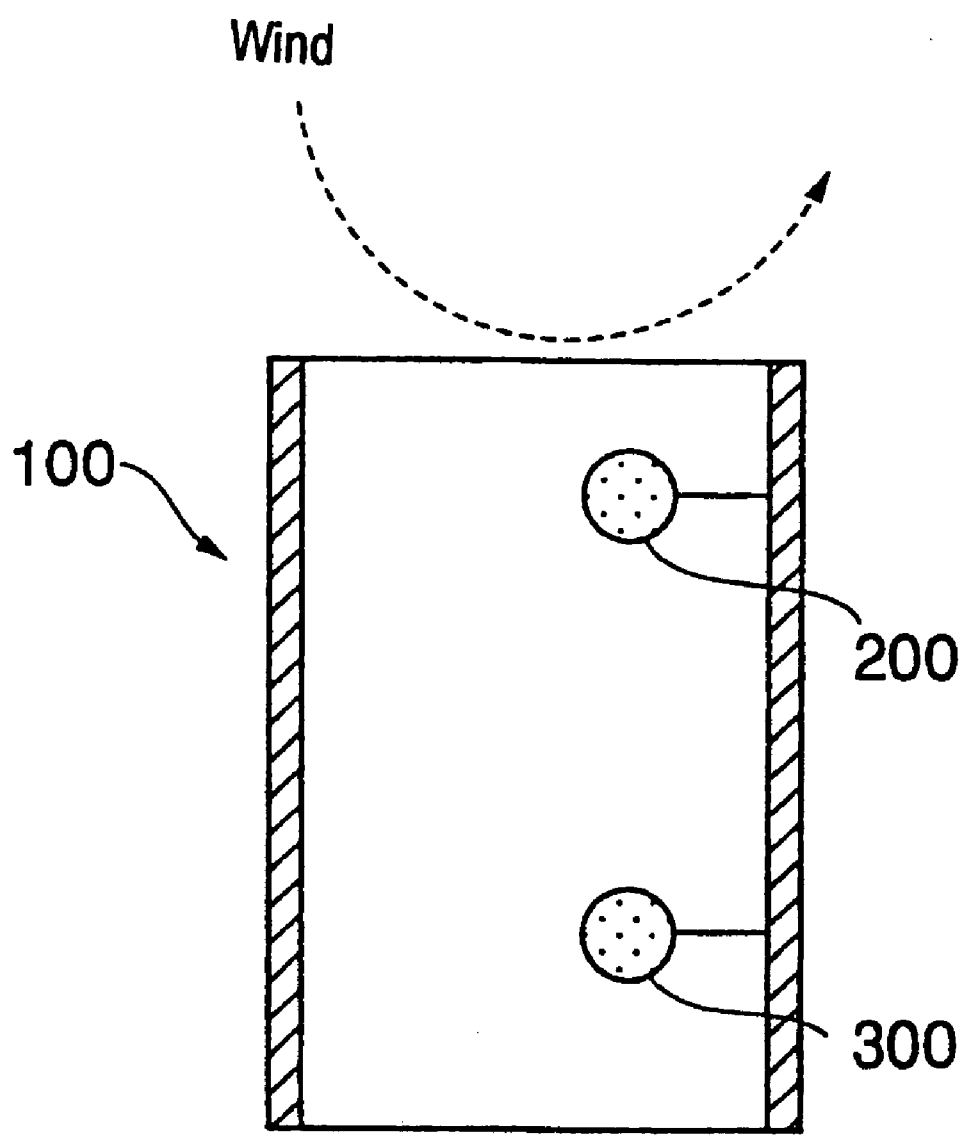
FIG. 19 is a schematic cross-sectional view illustrating a conventional apparatus.

By using the same apparatus as described above, transpiration amounts when blink was made at intervals of 5 seconds were measured. The results are as shown in FIG. 18. From the graph, it has been confirmed that a serrated change in the transpiration amount corresponded to the blink at intervals of 5 seconds. The present invention therefore makes it possible to exactly grasp the dynamic behavior of the water transpiration amount form the ocular surface.

What is claimed is:

1. In an apparatus for measuring a transpiration amount, said apparatus including a barrel-type body having a humidity sensor provided inside of said barrel-type body and opening portions on a top and a bottom of said barrel-type body, an improvement comprising:

a gas introductory path for feeding a gas having a predetermined water content, from an outside of said apparatus, to a surface to be measured, wherein said gas introductory path is disposed at a side wall portion of said barrel-type body of said apparatus, and a freely openable or closable shutter portion is installed at a bottom opening portion of said barrel-type body of said apparatus.

2. The apparatus according to claim 1, wherein said humidity sensor is disposed above an opening portion of the gas introductory path inside of said barrel-type body of said apparatus.

3. The apparatus according to claim 1, wherein said gas introductory path is formed by fixing an appropriate number of pipes, each of which opens at a position a little above an end of said bottom opening portion of said barrel-type body of said apparatus, to an inside surface of said barrel-type body of said apparatus.

4. The apparatus according to claim 1, wherein said shutter portion comprises a rotary slide plate.

5. The apparatus according to claim 1, wherein said shutter portion comprises a vertically movable lid.

6. The apparatus according to claim 1, wherein said barrel-type body of said apparatus is provided, inside thereof, with a temperature sensor.

7. The apparatus according to claim 1, wherein an eye-surrounding attachment for forming a closed space is disposed in connection with said bottom opening portion of said barrel-type body of said apparatus with said shutter portion being interposed therebetween.

8. The apparatus according to claim 7, wherein the gas introductory path is provided with a nozzle mechanism for filling an inside of said eye-surrounding attachment with the gas without directly injecting the gas to an ocular surface of said eye-surrounding attachment.

9. The apparatus according to claim 8, wherein said nozzle mechanism is formed by installing, below a lower opening portion of said gas introductory path, a gas collision plate equipped with a gas exhaust port, with a gas supplying space being disposed between said gas collision plate and an inside wall of said barrel-type body of said apparatus.

10. The apparatus according to claim 8, wherein said nozzle mechanism is formed by connecting, with a lower opening portion of said gas introductory path, a doughnut-shaped pipe having an appropriate number of nozzle holes opened toward an inside wall of said eye-surrounding attachment.

\* \* \* \* \*